US00PP34817P2

(12) United States Plant Patent
Warren et al.

(10) Patent No.: US PP34,817 P2
(45) Date of Patent: Dec. 13, 2022

(54) JAPANESE SNOWBELL TREE NAMED 'JFS 6SJ'

(50) Latin Name: *Styrax japonicus*
Varietal Denomination: 'JFS 6SJ'

(71) Applicant: J. Frank Schmidt & Son Co., Boring, OR (US)

(72) Inventors: Keith S. Warren, Gresham, OR (US); Guy E. Meacham, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 17/714,492

(22) Filed: Apr. 6, 2022

(51) Int. Cl.
*A01H 5/02* (2018.01)
*A01H 6/00* (2018.01)

(52) U.S. Cl.
USPC ..... Plt./216
CPC ..... *A01H 6/00* (2018.05)

(58) Field of Classification Search
USPC ..... Plt./216
CPC ..... A01H 6/00
See application file for complete search history.

*Primary Examiner* — Anne Marie Grunberg
(74) *Attorney, Agent, or Firm* — Klarquist Sparkman, LLP

(57) ABSTRACT

A variety of *Styrax japonicus* which combines a combination of a mounding weeping habit, profuse single white flowers, dark purple foliage that remains glossy & disease free through the summer.

11 Drawing Sheets

Latin name of the genus and species of the plant claimed: *Styrax japonicus*.

Variety denomination: 'JFS 6SJ'.

BACKGROUND OF THE INVENTION

In 2003 we began a program on ornamental Japanese snowbell cultivar development. One of the goals of the program was to produce an improved cultivar with weeping form. In 2005 a large number of seedlings were grown in nursery rows in Boring, Oreg. The best were transplanted for further evaluation in 2007, and then selected again for their best features. The most promising selections included trees with weeping form and were transplanted into a final evaluation block in 2011. Next to these trees, we planted a single specimen of *Styrax japonicus* 'Evening Light' U.S. Plant Pat. No. 24,168.

We allowed these trees to freely cross pollinate in the spring of 2012, and then in the fall of 2012, collected the seed of the 'Evening Light' as well as other selected individual trees in the block. This seed collection produced a total of 166 plants grown in small liner pots in 2013.

In the spring of 2014 these seedlings from four different parent trees were planted out in a trial row for observation and evaluation. By 2015 it was clear to see that one of the seedlings of 'Evening Light' exhibited a unique set of characteristics: Similar dark purple foliage to the parent tree *Styrax japonicus* 'Evening Light' but having a strongly weeping instead of upright growth habit. This tree was labelled 'JFS 6SJ' and tagged for further observation & evaluation.

In the summers of 2015 and 2016 we took cutting wood from this tree and 96 softwood cuttings were made each year to assess its ability to be propagated from cuttings as well as from budding. Liners produced from these cuttings were planted out in 2017 & 2018 for observation & evaluation.

Also in the summer of 2016 budwood was taken from 'JFS 6SJ' and we budded onto 15 seedlings. 7 of these buds were successful and produced new trees. Observations continued of both the original tree and these new trees.

In 2017 this budding process was repeated with 120 trees producing a further 79 trees for evaluation.

All cuttings taken from 'JFS 6SJ' for asexual propagation were rooted under mist and grown in Boring, Oreg. All buds taken from 'JFS 6SJ' were budded onto rootstocks and grown in Boring, Oreg.

By 2018 it was clear to see that 'JFS 6SJ' could be successfully asexually propagated by both softwood cutting production and field chip budding. Both methods produced trees that exhibited the exact same characteristics as the original tree in every respect.

In 2018 the original 'JFS 6SJ' was transplanted into a new location on the nursery where it remains today. Of the test trees that were produced 50 were kept as stock trees and planted into field stock block locations in 2020 to provide stock material for future production. The remaining test trees were destroyed.

BRIEF SUMMARY OF THE INVENTION

This new cultivar possesses a unique combination of characteristics that have proven firmly fixed in asexually propagated progeny and that comprise a combination of a dark purple foliage, white flowers and a pendulous or weeping form.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
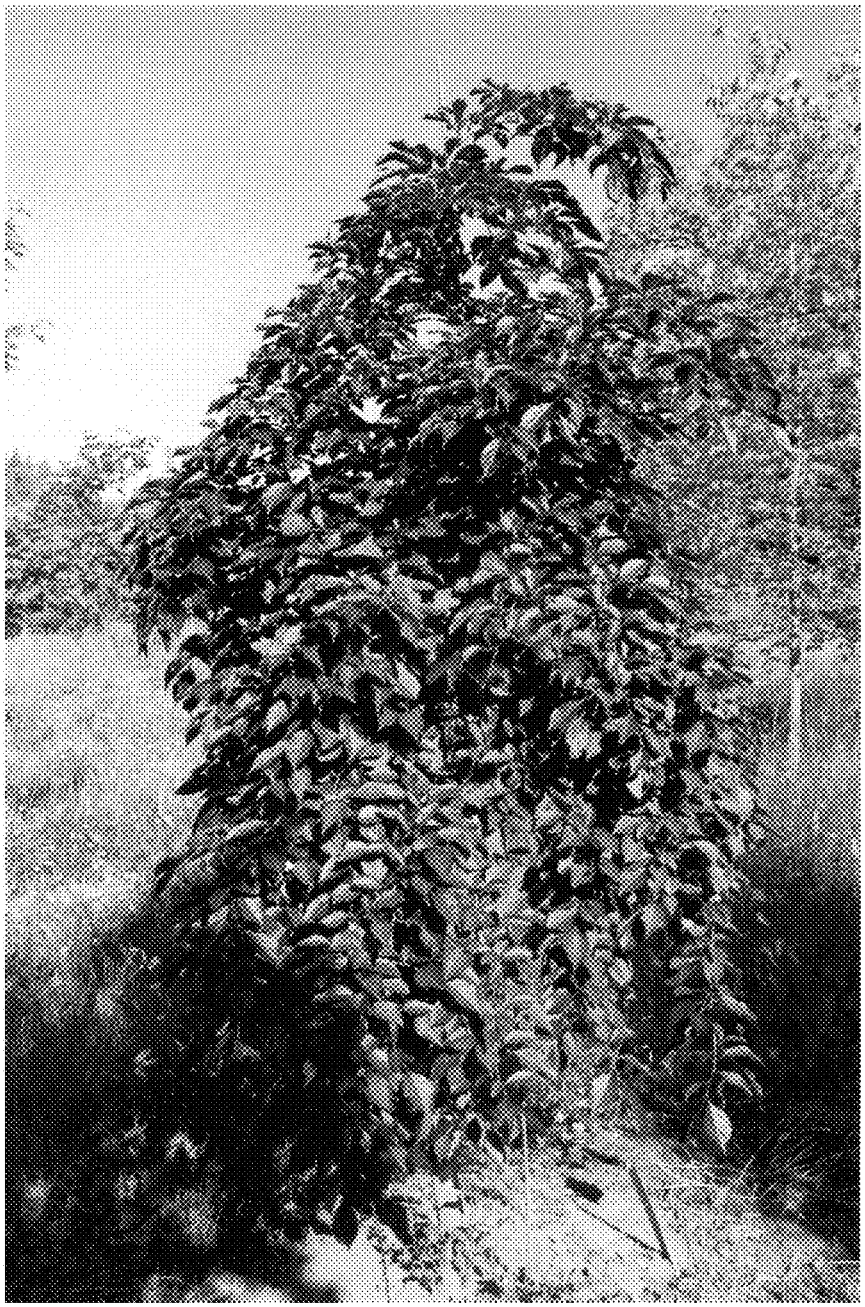
FIG. 1: Shows the original tree at 8 years of age with summer foliage.
Figure 2:
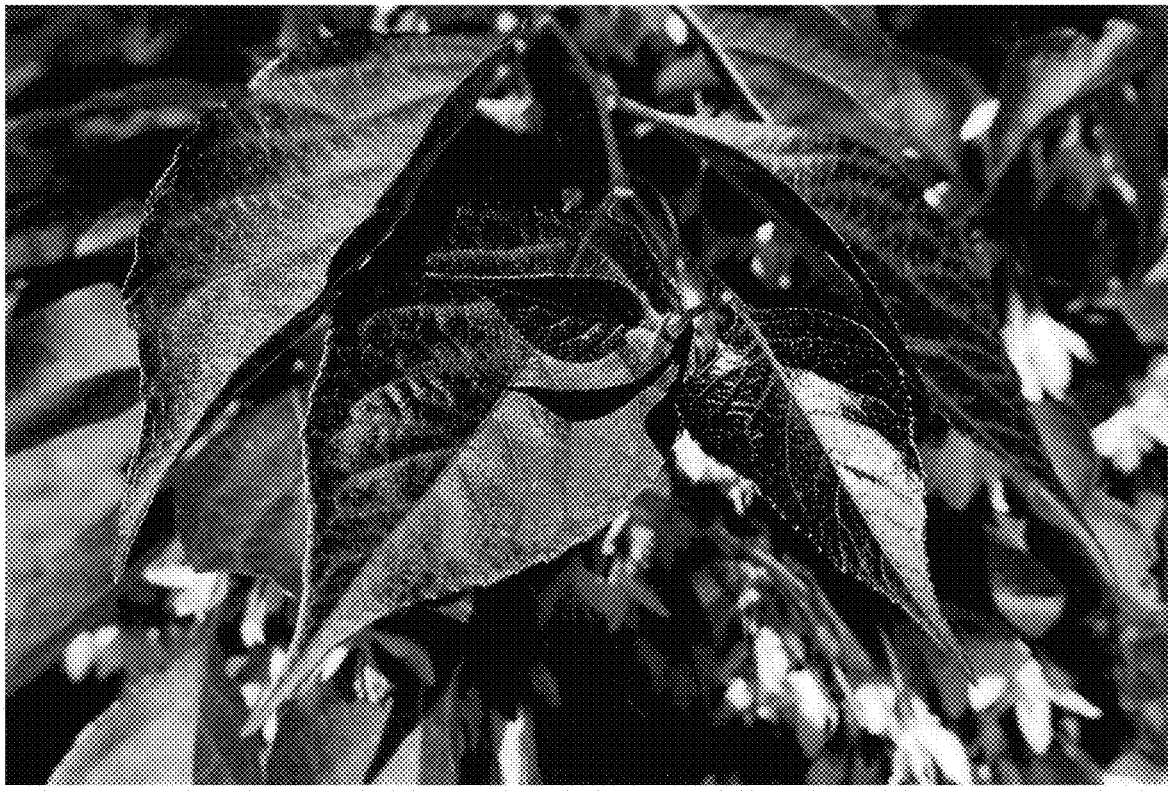
FIG. 2: Shows a close-up of the spring foliage on the original tree.
Figure 3:
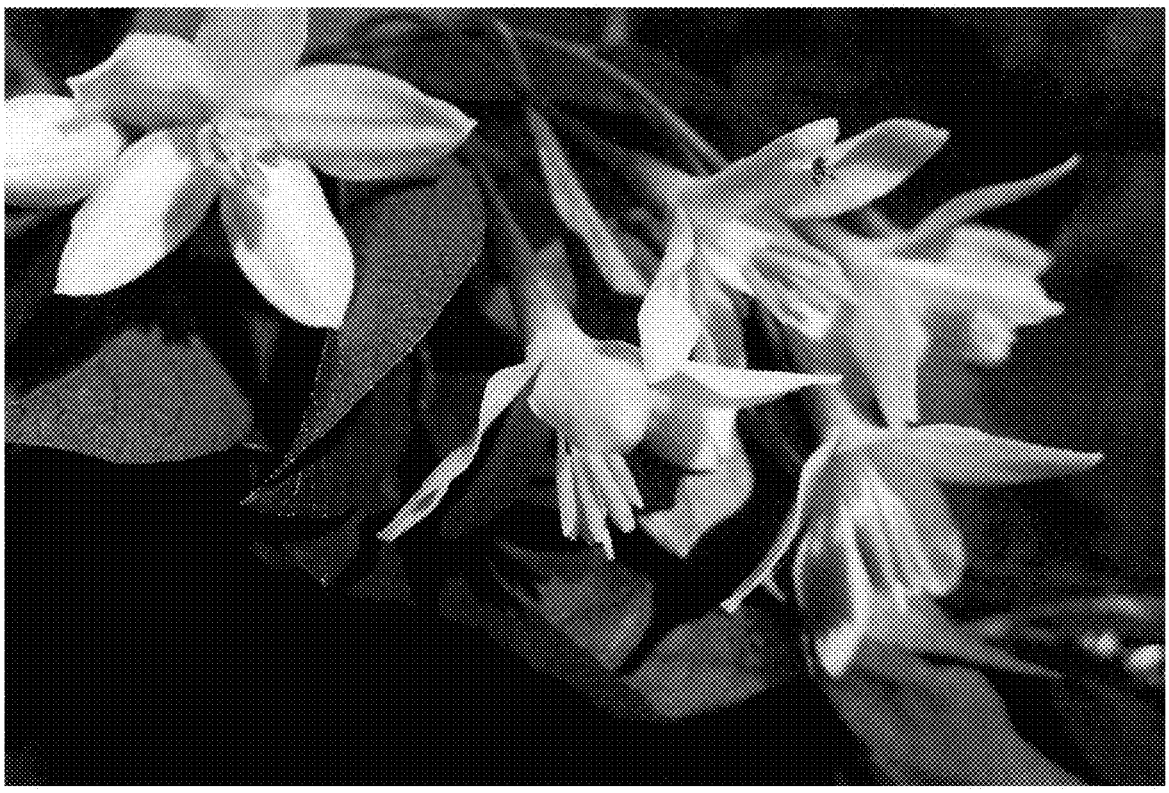
FIG. 3: Shows a close up of flowers on the original tree.
Figure 4:
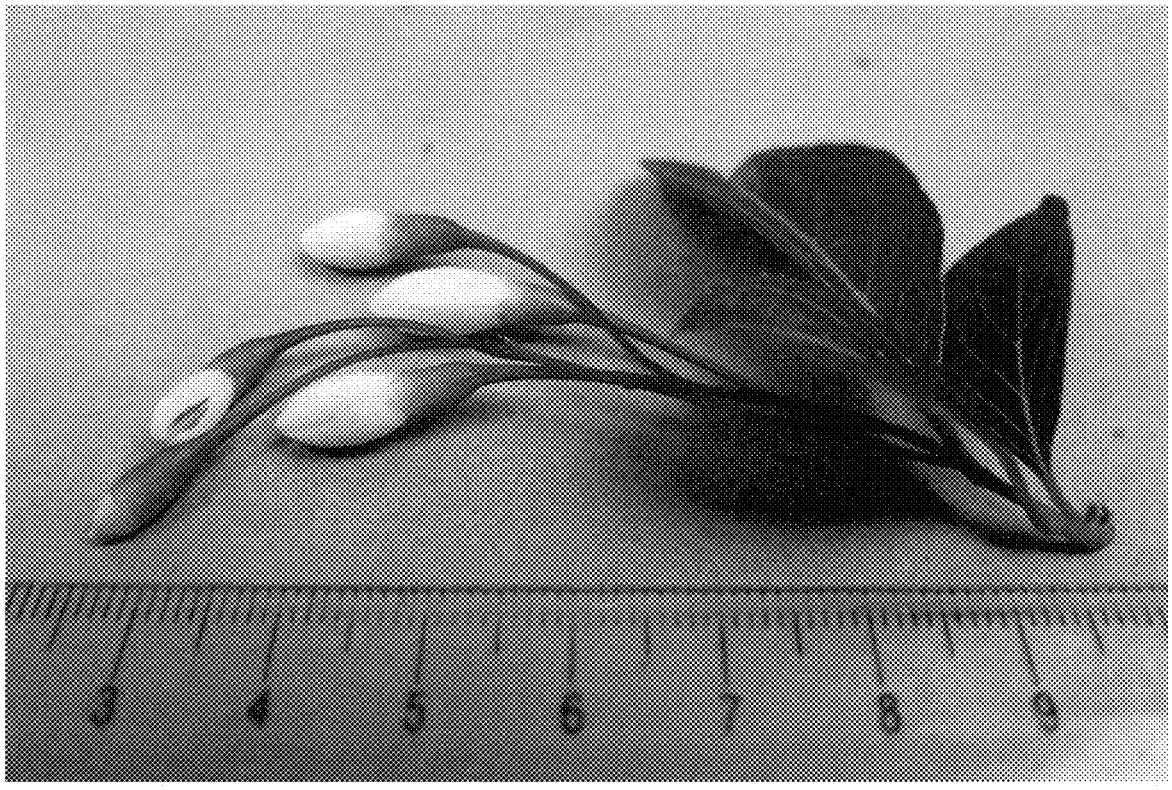
FIG. 4: Shows a close up of flower buds on a display board with scale.
Figure 5:
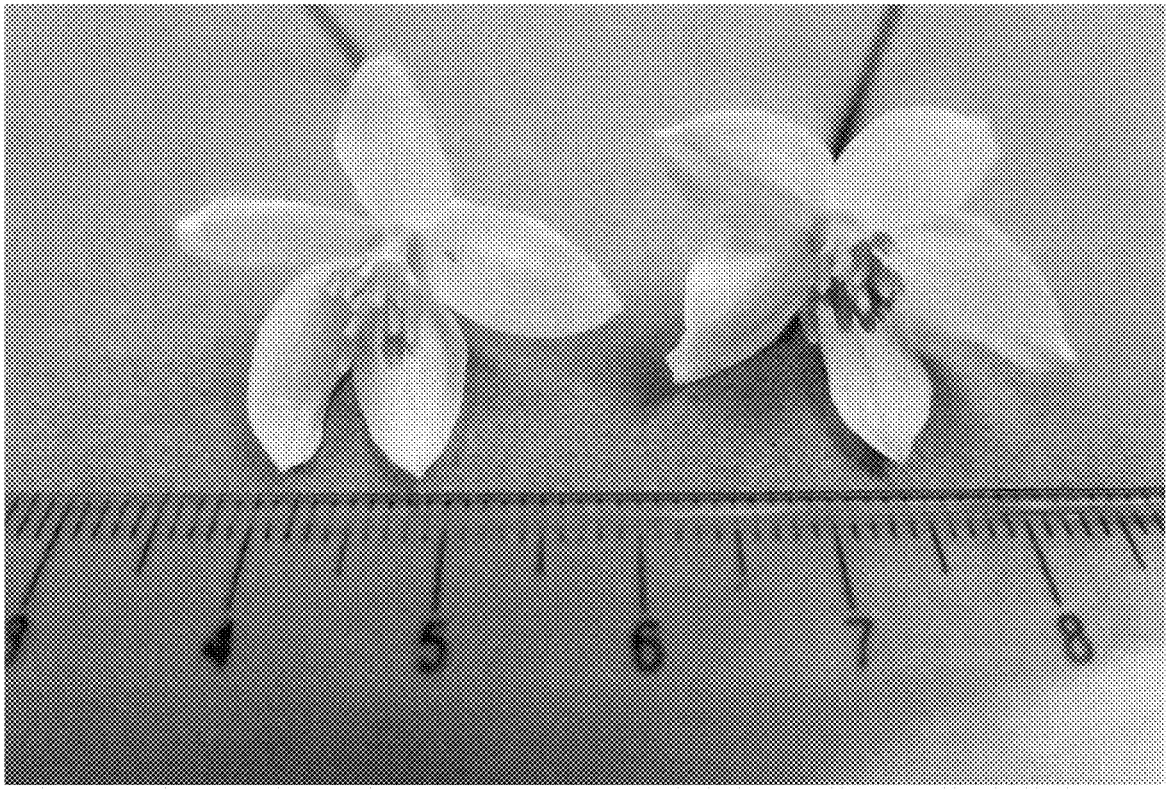
FIG. 5: Shows a close up of flowers on a display board with scale.
Figure 6:
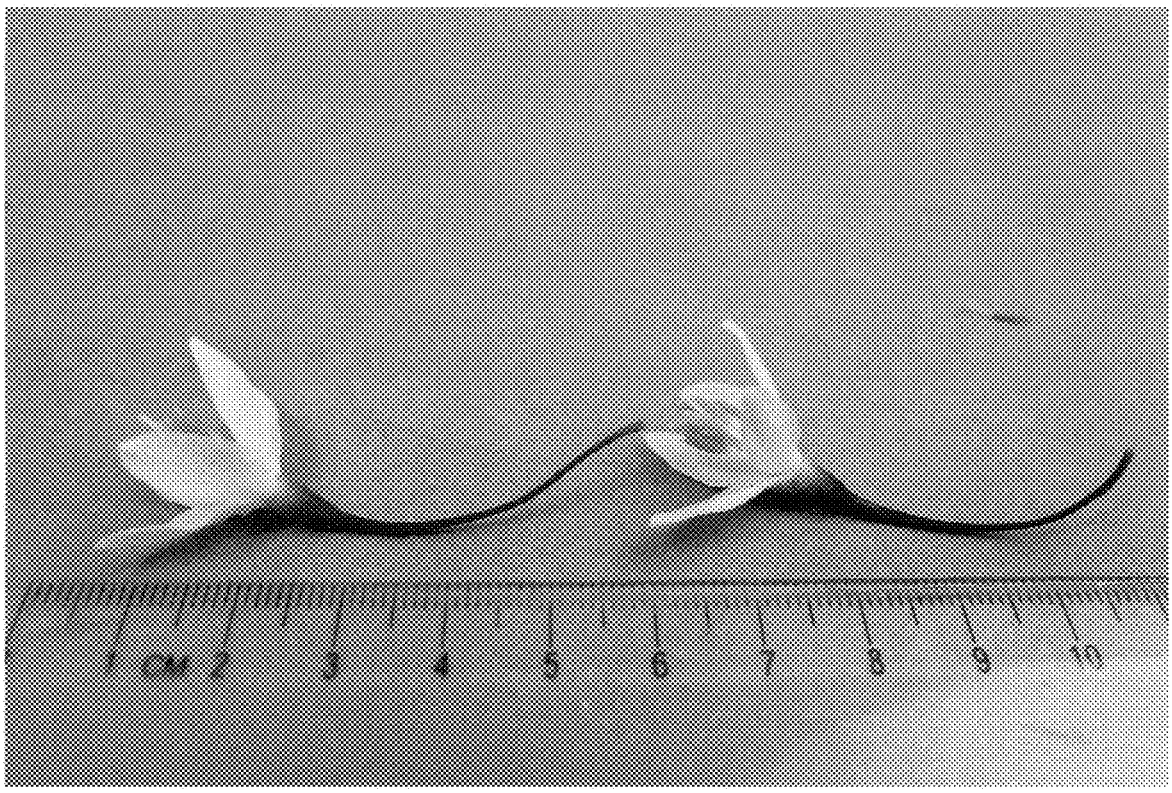
FIG. 6: Shows a close up of flowers on a display board with scale.
Figure 7:
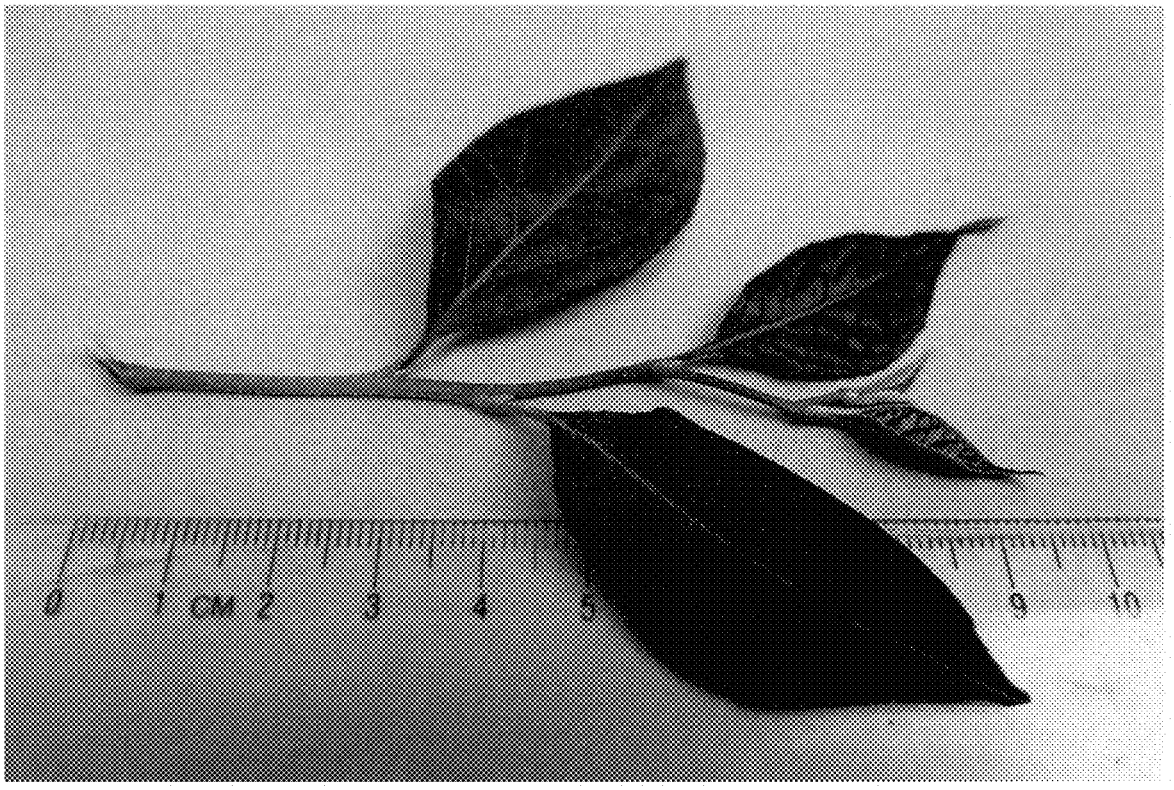
FIG. 7: Shows new spring foliage tip on a display board with scale.
Figure 8:
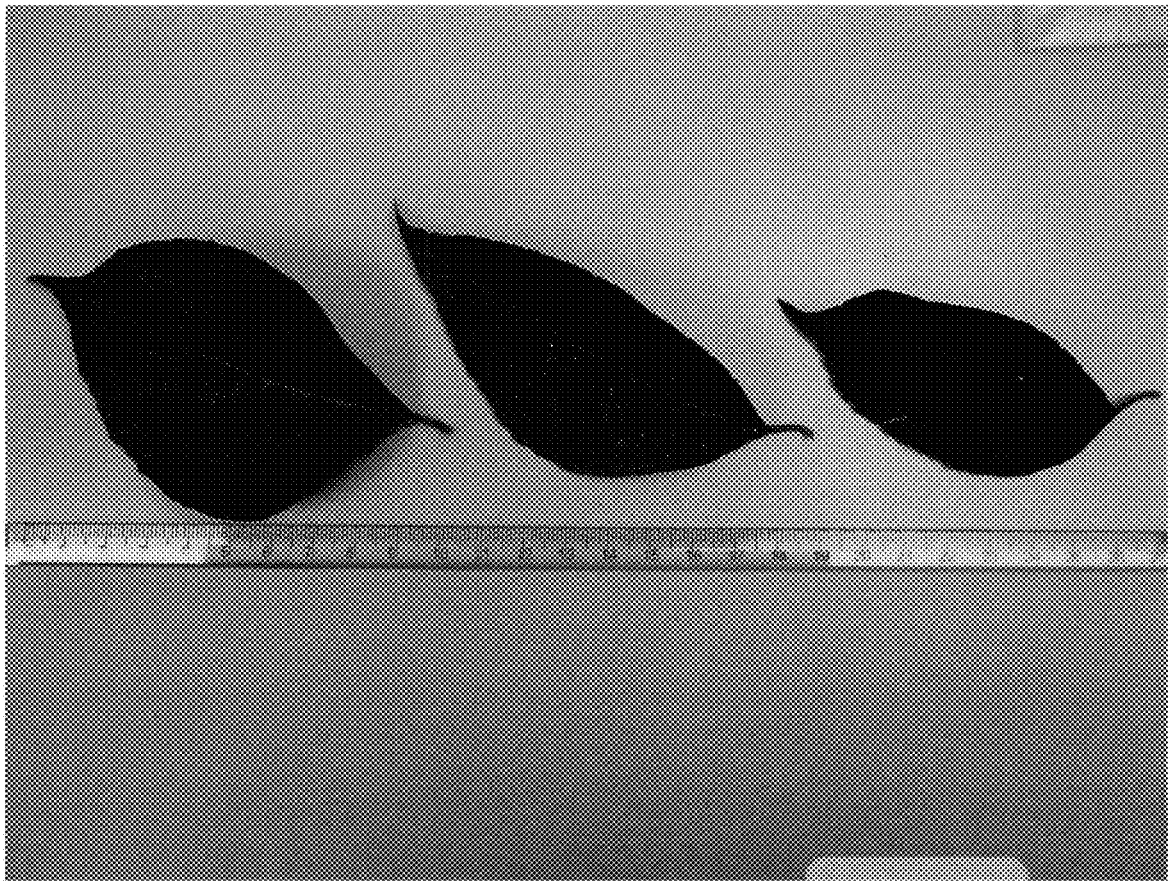
FIG. 8: Shows autumn leaves on a display board with scale.
Figure 9:
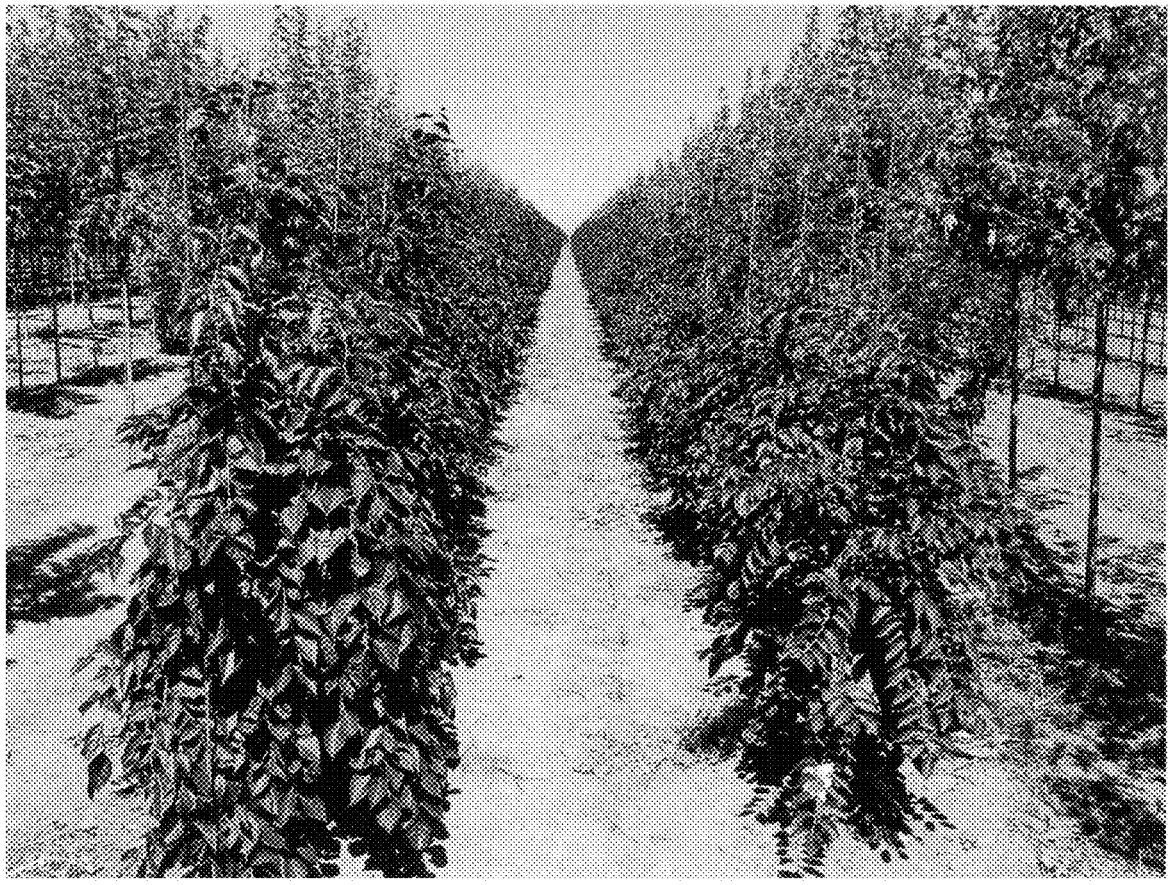
FIG. 9: Shows 3 year old trees in nursery row production.
Figure 10:
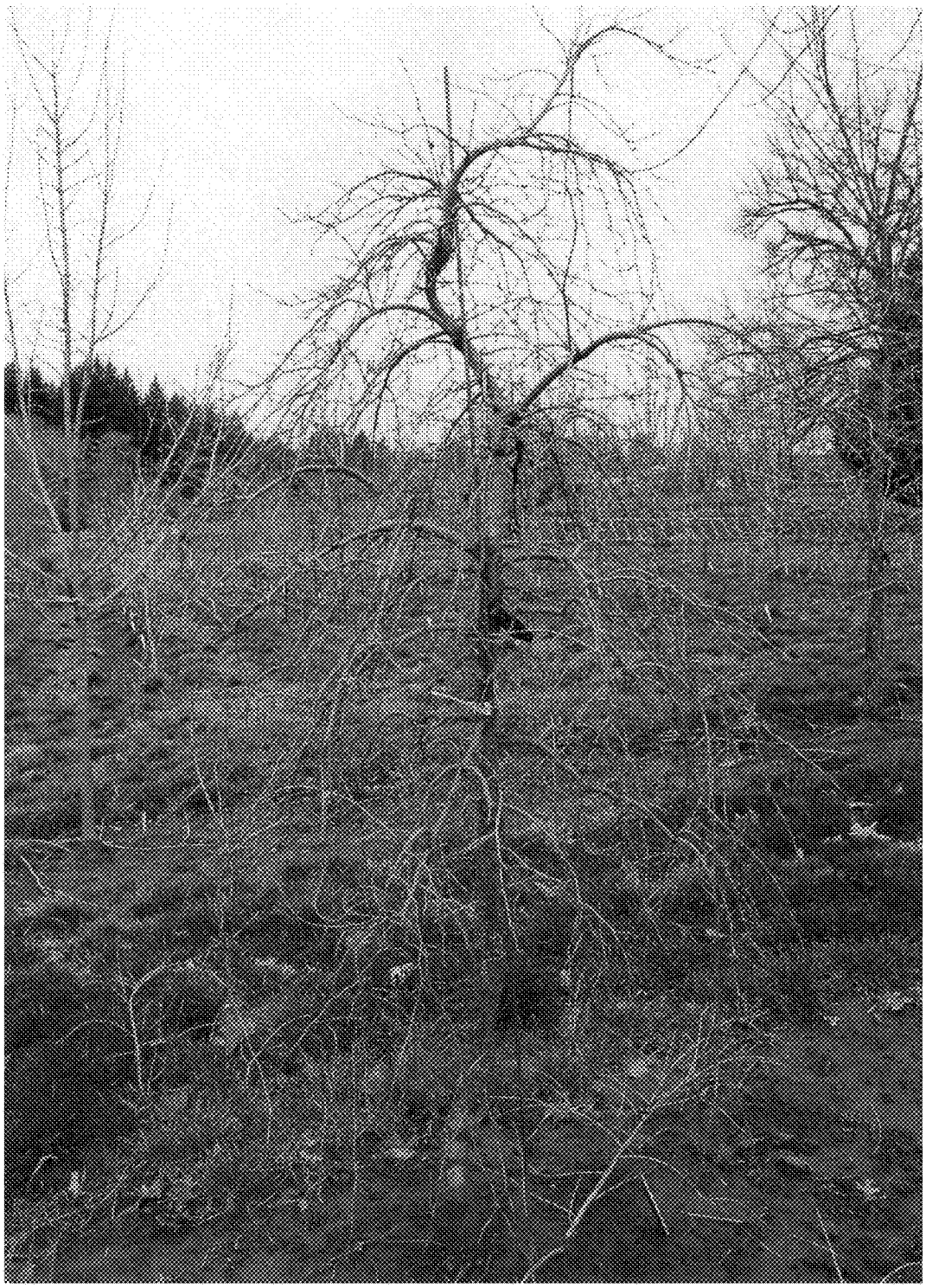
FIG. 10: Shows the original tree in winter without foliage.
Figure 11:
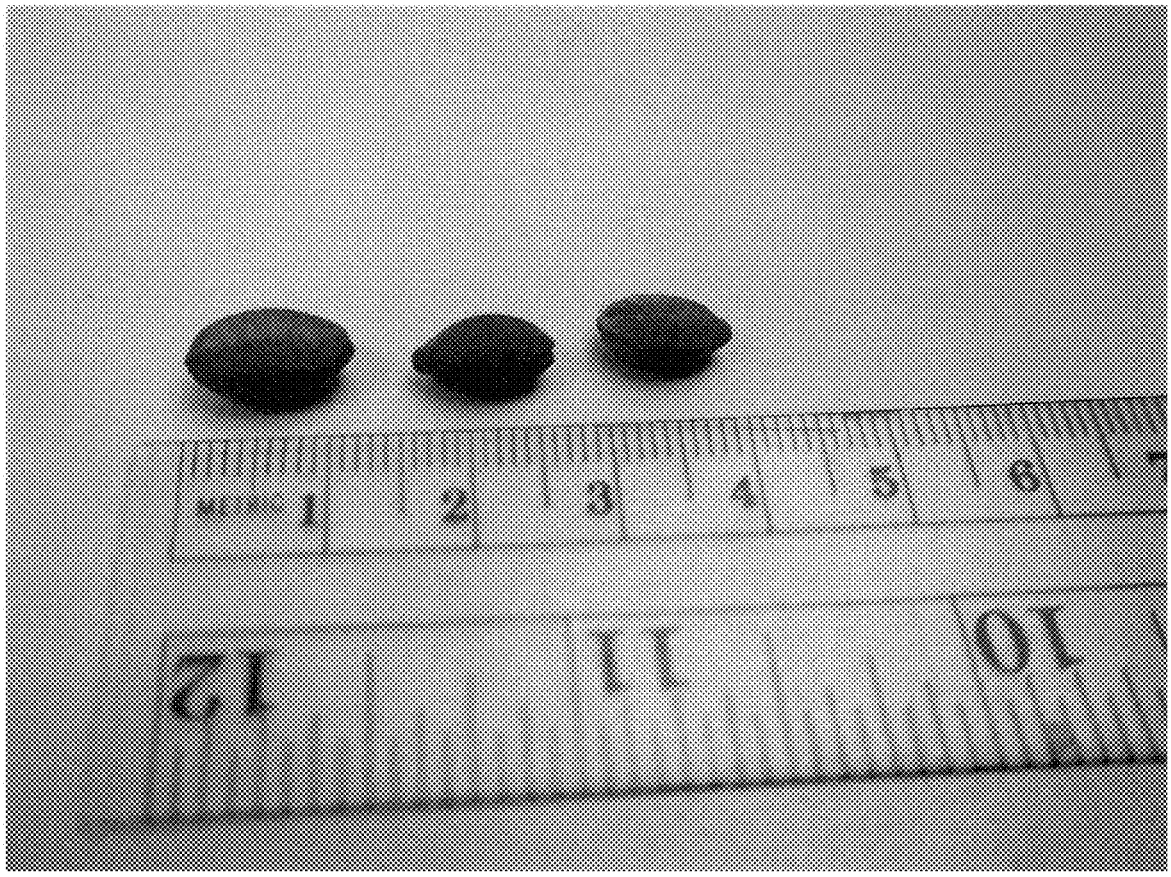
FIG. 11: Shows seed on a display board with scale.

The following detailed description of the 'JFS 6SJ' variety is based on observations of the original tree growing in Boring, Oreg. and of two and three year old asexually reproduced progeny. The observed progeny were trees which were growing in Boring, Oreg. Color descriptions are made with reference to The Royal Horticultural Society (London) Colour Chart © 1986, except where ordinary dictionary significance of color is indicated.

Scientific name: *Styrax japonicus* 'JFS 6SJ'.

Parentage:

*Seed parent*.—Open pollinated seedling of *Styrax japonicus* 'Evening Light' U.S. Plant Pat. No. 24,168.

*Pollen parent*.—Unknown.

Tree:

*Overall shape*.—Upright with pendulous branching.

*Height*.—At 9 years of age, about 2.5 meters high.

*Width*.—At 9 years of age 1 meter spread.

*Caliper* (*trunk diameter*).—At 9 years of age, about 85 mm at 100 mm height, 65 mm at 1 m height.

*Trunk*.—Strong with curves under nursery growing conditions.

*Trunk bark texture*.—Smooth with longitudinal shallow fissures.

*Trunk bark color*.—Greyed Green 197B.

*Immature bark color*.—Greyed Orange 163D.

*Mature bark color*.—Greyed Green 197C to 198B.

*Lenticels*.—Absent.

*Branch color*.—Greyed Brown 199A.

*Branch lenticels*.—Absent.

*Dormant buds*.—Sessile 3-4 mm long 1-1.5 mm wide.

*Internodes*.—Average internode length is about 15-25 mm on one-year-old shoots.

*Hardiness*.—Has tolerated temperatures to 14° F. in Boring, Oreg. (Jan. 6, 2017) which is the lowest temperature experienced at this location for this period. It is believed to have zone 5 cold hardiness similar to other plants of the same species.

Leaves: Except as otherwise noted, observations are from twenty vigorous growth leaves.

*Arrangement*.—Alternate.

*Type*.—Simple, entire.

*Texture*.—Smooth, with slight undulation between the veins.

*Sheen*.—Glossy on upper surface Matt on the lower surface.

*Length*.—Averaging 60 mm-90 mm.

*Width*.—Averaging 20 mm to 40 mm.

*Petioles*.—8 mm to 10 mm long, about 1-2 mm in diameter.

*Overall shape*.—Ovate.

*Margin*.—Serrulate.

*Tip*.—Acuminate.

*Base*.—Acute.

*Spring leaf color*.—Greyed-Purple 187A to 187B.

*Summer leaf color*.—Greyed-Purple 187A fading to Green 139A. Lower leaf surface: Green 137A to 137B. Vein: Greyed-Purple 187C. Fall Leaf Color: Foliage returns to Greyed-Purple 187A fading to Brown 200A.

*Fall color begins*.—October 15th (Boring, Oreg. 2021).

*Fall color peak*.—November 1st (Boring, Oreg. 2021).

*Fall color ends*.—November 20th (Boring, Oreg. 2021).

*Pubescence*.—None.

*Persistence*.—Tree is deciduous.

Flowers:

*Overall*.—Number of flowers per cluster: 4 to 5.

*Size*.—24 mm to 28 mm in diameter.

*Shape*.—Symmetrical, rounded, 5 petals, not cupped.

*Unopened bud*.—Red Purple 65B to Red Purple 65C.

*Petals*.—Five petals per flower, 6 mm to 8 mm wide× 15 mm to 18 mm long. Color White 155A to very pale Red-Purple 62D.

*Stamens*.—About 10 to 15 stamens, 8 mm to 10 mm arranged concentrically around pistil.

*Anthers*.—Orange 26A. 2 mm to 3 mm long by 0.5 mm to 1 mm in diameter.

*Pistil*.—Yellow 10A, length 8 mm-10 mm.

*Pollen*.—Orange 26A.

*Pedicel*.—20 mm to 30 mm long by 0.5 mm to 0.6 mm in diameter. Red 46A.

*Pubescence*.—None.

*Fragrance*.—Slightly sweet.

*Flowering date*.—In Boring, Oreg. 2021 (an average bloom year). First bloom May 15th, peak bloom May 30th, last bloom June 15th.

Fruit: Observations are from a sampling of typical seeds.

*Cluster*.—4 to 5 seeds per cluster.

*Type*.—Dried drupe, ovoid, longer than wide.

*Size*.—Typical fruit is 8 mm to 10 mm in length by 6 mm to 8 mm wide.

*Color*.—Immature fruit is Greyed-Green 194A to 194C.

*Seeds*.—Typically 1 per fruit, ovoid 6 mm to 8 mm long by 5 mm to 6 mm wide.

*Seed color*.—Mature seed is Greyed — Orange 164A to 164B.

COMPARISON TO THE SEED PARENT

Compared to the seed parent tree *Styrax japonicus* 'Evening Light' the claimed cultivar 'JFS K6SJ' has a very different growth habit having pendulous weeping branches rather than an upright growing habit.

COMPARISON TO OTHER SIMILAR VARIETIES:

| | *Styrax japonicus* 'JFS 6SJ' | *Styrax japonicus* 'Evening Light' U.S. Plant Pat. No. 24,168 | *Styrax japonicus* 'JL Weeping' U.S. Plant Pat. No. 23,755 |
|---|---|---|---|
| Form | Pendulous Growth | Upright Growth | Pendulous Growth |
| Leaf Color | Purple | Purple | Green |
| Leaf Length | 60 mm to 90 mm | 40 mm to 70 mm | 80 mm to 100 mm |
| Flowers | Single. White 155A to Red-Purple 62D | Single. White 155B | Single. Red - Purple 65B |

-continued

COMPARISON TO OTHER SIMILAR VARIETIES:

| | *Styrax japonicus* 'JFS 6SJ' | *Styrax japonicus* 'Evening Light' U.S. Plant Pat. No. 24,168 | *Styrax japonicus* 'JL Weeping' U.S. Plant Pat. No. 23,755 |
|---|---|---|---|
| Comparative flowering time | Late May to Mid June in Boring Oregon | Late May to Mid June in Boring Oregon | Mid to late May in Boring Oregon |

We claim:

1. A new and distinct variety of Japanese snowbell tree as herein illustrated and described.

* * * * *